United States Patent
Michael

(10) Patent No.: US 8,249,266 B2
(45) Date of Patent: Aug. 21, 2012

(54) FILTER SYSTEM FOR HEARING PROTECTION DEVICE FOR CONTINUOUS NOISE EXPOSURE MONITORING

(75) Inventor: Kevin Michael, Pittsburgh, PA (US)

(73) Assignee: Sperian Hearing Protection, LLC, San Diego, CA (US)

(*) Notice: Subject to any disclaimer, the term of this patent is extended or adjusted under 35 U.S.C. 154(b) by 2001 days.

(21) Appl. No.: 11/130,186

(22) Filed: May 17, 2005

(65) Prior Publication Data

US 2005/0254666 A1 Nov. 17, 2005

Related U.S. Application Data

(60) Provisional application No. 60/571,510, filed on May 17, 2004.

(51) Int. Cl.
| | |
|---|---|
| *A61F 11/06* | (2006.01) |
| *G10K 11/16* | (2006.01) |
| *H04R 1/10* | (2006.01) |
| *H04R 25/00* | (2006.01) |

(52) U.S. Cl. .......... 381/72; 381/71.5; 381/71.6; 381/74; 381/312; 381/328

(58) Field of Classification Search ............ 381/72, 381/71.6, 328, 74, 71.5, 312
See application file for complete search history.

(56) References Cited

U.S. PATENT DOCUMENTS

| 3,578,104 | A | * | 5/1971 | Sotome ...................... 181/164 |
|---|---|---|---|---|
| 4,674,161 | A | * | 6/1987 | Edinger et al. .............. 29/25.35 |
| 5,113,967 | A | * | 5/1992 | Killion et al. ................ 181/132 |
| 5,631,965 | A | * | 5/1997 | Chang et al. .................... 381/72 |
| 5,917,923 | A | * | 6/1999 | Caron et al. .................. 381/345 |
| 6,456,199 | B1 | | 9/2002 | Michael |
| 2001/0005421 | A1 | * | 6/2001 | Harris ........................ 381/332 |
| 2002/0080979 | A1 | * | 6/2002 | Brimhall et al. ................ 381/72 |

* cited by examiner

*Primary Examiner* — Devona Faulk
*Assistant Examiner* — George Monikang
(74) *Attorney, Agent, or Firm* — Conley Rose, P.C.; Kristin Jordan Harkins

(57) ABSTRACT

A hearing protection device to be worn at either a primary position or a secondary position, comprising a hearing protection component and a noise measurement component, and an attachment mechanism to securely attach the noise measurement component to the hearing protection component, wherein at the primary position the noise measurement component detects a protected noise exposure and at the secondary position it detects an unprotected exposure, the noise measurement component comprises a microphone, a compartment that encloses the microphone and at least one filter, and the filter reduces resonance of said compartment incident upon said microphone.

20 Claims, 2 Drawing Sheets

FILTER SYSTEM FOR HEARING PROTECTION DEVICE FOR CONTINUOUS NOISE EXPOSURE MONITORING

CROSS REFERENCE TO RELATED APPLICATIONS

This application claims the priority of U.S. Provisional Application No. 60/571,510, filed May 17, 2004, the disclosure of which is expressly incorporated by reference herein.

BACKGROUND OF THE INVENTION

Long-term exposure to high levels of noise may cause hearing loss and other health hazards, and as a consequence U.S. law requires that the noise exposure level of an individual in a work place be accurately measured. See e.g. 29 C.F.R. §1910.95, and U.S. Pat. No. 6,456,199 for a general discussion. A noise dosimeter with the microphone located near the workers' shoulder is commonly used in the industry to measure the individual cumulative noise exposure over the course of a full work shift. Since the microphone is located on the shoulder, the measurements do not account for any noise reduction afforded by hearing protectors and therefore the measurement quantity is unprotected individual exposure.

Hearing protectors are commonly used in industry to reduce the level of noise incident on the ear of the worker. U.S. Pat. No. 6,456,199, incorporated herein by reference, discloses a cost-effective and unobtrusive means of continuously monitoring a hearing protector wearer's actual, protected, noise exposure rather than simply measuring unprotected individual exposure.

The monitoring system includes at least one microphone, housed in the interior of a hearing protective device. Exposure dosage calculation includes periods when the HPD is worn (primary microphone position) and periods when it is not worn (secondary microphone position). When the HPD is worn at the primary position, it measures the noise level with the protective device in effect, and when the HPD is worn at the secondary position, it measures the noise level of the environment without the protective device. This provides an accurate measurement of the actual cumulative exposure dosage because invariably workers have their hearing protectors donned for part of the day and removed for part of the day.

DESCRIPTION OF THE INVENTION

In order to accurately measure the noise level, it is important to measure the noise equally at all sound frequencies. Also, the measurement device itself should not distort the frequency spectrum of the sound or noise to be measured. Toward that end, it is desirable to design microphones to capture all frequency components equally, and as such are referred to as 'flat' response microphones. For example, the Panasonic® WM60 Electret microphone is such a flat response microphone across the audible frequency range.

Enclosing a microphone in a compartment, such as a holder, however, alters the acoustic characteristics of the system. For example, one feature of the system described in U.S. Pat. No. 6,456,199 is a microphone holder, the construction of which effectively creates a chamber in front of the measurement surface of the microphone. This chamber adds a resonance to the microphone. In other words, an artificial emphasis is created on the signal in a specific frequency range, which is referred to as the resonant frequency.

Figure 2:
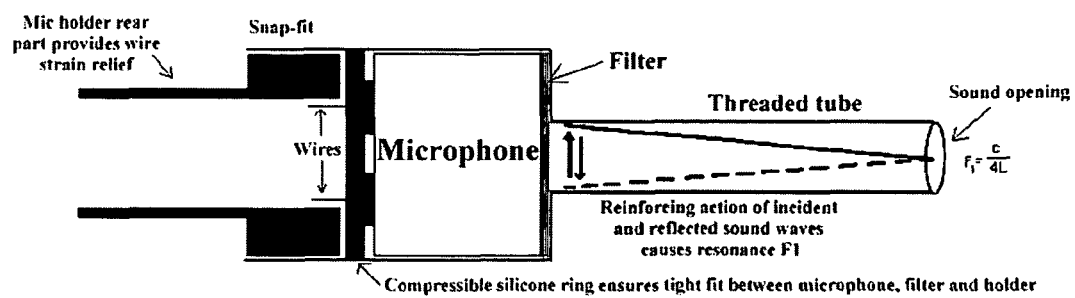
FIG. 2 illustrates schematically an embodiment of a hearing protection device with noise measurement.

The microphone holder is essentially an acoustic duct with one open end and one sealed end. The sealed end has an almost infinite impedance to the acoustic signal. The infinite impedance results in 100% reflection of incoming sound waves. Therefore sound waves are traveling toward the microphone surface from the open end and away from the microphone surface due to the reflection. The sound waves traveling in opposite directions in the narrow channel result in 'standing acoustic waves', or areas where the sound waves reinforce each other, resulting in sound amplification at the 'resonant' frequencies (see FIG. 2 for example).

The resonant frequency (F) equals to the speed of sound (C) in air divided by four times the tube length (L). Thus:

$$F=C/4L.$$

Additionally, the earplug component is screwed onto the microphone holder_tip, which effectively increases the length of the tube, affecting the resonance.

For the example of an earplug/microphone holder assembly, the closed end of the tube is the microphone measurement surface and the open end is the open end of the earplug. If the length of the microphone holder/earplug tube is 0.019 meters, the resonant frequency is be about 4.5 kHz.

This resonance should be minimized as much as possible to maintain accuracy of the overall system. Otherwise, the existence of a significant component in the 4.5 kHz frequency range will cause the microphone readings to be about 5-10 dB higher than the actual ambient levels. This occurs since the sound waves in this frequency range are reinforcing each other causing amplification within the sound pathway. This exaggeration of the noise exposure level could lead to unnecessary implementations of administrative controls or engineering noise controls. Also, if these readings were used to determine compliance with noise regulations, the workplace could be found in violation of the specified regulations when in fact the ambient levels were within prescribed limits.

Additional resonant frequencies also exist at three, five, and seven times this frequency (and so on) since the sound waves are reinforcing each other at these frequencies causing higher levels within the sound tube. However, these resonant frequencies exceed the range of human hearing so they are not of interest.

The present invention provides a means to cancel this undesired amplification. According to one embodiment of the present invention, an acoustic filtering system is provided that decreases the impedance of the sealed end of the sound tube, thereby significantly reducing the reflection of sound away from the microphone surface. Reducing the reflections away from the microphone surface reduces the sound reinforcement within the sound tube. Another important characteristic of the filter is that it must not significantly attenuate other frequencies in the measurement frequency range (from 50-10000 Hz). Again, this attenuation would lead to distortion of the sound signal, leading to inaccurate measurements. Since high frequency sound is typically attenuated by barriers more easily than lower frequency sound, this is a particular problem at the higher frequency range.

With the filter mechanism, the sound reaching the microphone diaphragm via the holder/plug/filter pathway is essentially equivalent to the sound that the microphone would sense with no holder present.

In one embodiment, the hearing protection device of the present invention comprises a hearing protection component and a noise measurement component, and an attachment mechanism to securely attach the noise measurement component to the hearing protection component. The noise measurement component comprises a microphone, a compartment that encloses the microphone and at least one filter, and the filter reduces resonance of said compartment incident upon said microphone.

Figure 1:
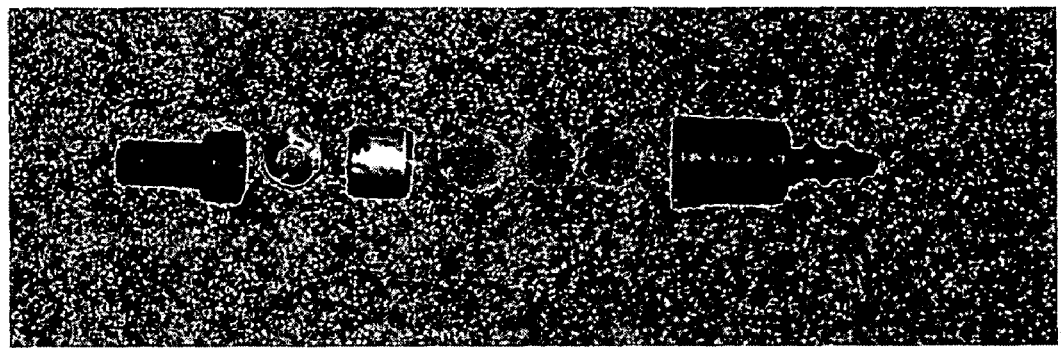
FIG. 1 illustrates the components of an exemplary embodiment of a hearing protection device with noise measurement.

Preferably, the hearing protection device comprises a microphone holder, which comprises two molded plastic parts, a front part and a rear part (see FIG. 1). The front part houses the microphone and filters, and provides an attachment mechanism to securely attach to the insert-type earplugs. The attachment mechanism includes a screw-thread on the holder tip. A channel through the middle of the plugs provides both a sound pathway for sampling the noise level and a mechanism for attaching the screw tip of the holder to the plug. The rear part of the microphone holder permanently snap-fits to the front part, using a silicone ring to securely hold the microphone in place. The rear part of the microphone holder assembly also provides a strain-relief to the microphone wire.

The filter system of the current invention comprises one or more layers of sound absorbing materials that eliminates or reduces acoustic reflections from the sealed end of a tube without affecting the incoming signal at other frequencies. The reduction of reflections occurs since the sound waves are absorbed by the material with the acoustic energy converted to heat. Many filter materials suitable for the filter system of the present invention are known in the art. Practically, preferable filter materials should be inexpensive, easy to manufacture and process for assembling into the hearing protecting device. The filter materials will be shaped to fit into a tube and cover the face of the microphone. The material should not be bulky and have a useful, field life of 6-12 months.

Preferably, the filter system is made of layers of suitable cloth materials. Generally speaking, cloth made of synthetic fibers are more preferred over natural fibers, because they are not subject to infestation by microorganisms or insects, and are more hygienic.

In one particularly preferred embodiment, the filter system of the present invention comprises three layers of a polyester-cloth material snuggly fitted to the surface of the microphone.

In summary, the current invention consists of a snap-fit molded plastic microphone holder. The holder contains an acoustic filter that damps the resonance of the holder screw tip without affecting other frequency ranges, thus essentially restoring the original acoustic signal to the microphone measurement surface.

What is claimed is:

1. A hearing protection device to be worn at either a primary position or a secondary position, comprising a hearing protection component and a noise measurement component, and an attachment mechanism to securely attach the noise measurement component to the hearing protection component, wherein
   at the primary position the noise measurement component detects a protected noise exposure and at the secondary position it detects an unprotected exposure,
   the noise measurement component comprises a microphone having a face, a compartment that encloses the microphone and at least one filter,
   the filter comprises one or more pieces of polyester cloth snuggly fit to the face of the microphone, and
   the filter minimizes resonance at a frequency of about 4.5 kHz without significantly attenuating other frequencies incident upon the face of the microphone.

2. The hearing protection device according to claim 1, wherein the filter substantially eliminates resonance of said compartment.

3. The hearing protection device according to claim 1, wherein the hearing protection component is an insert-type earplug.

4. The hearing protection device according to claim 3, wherein the attachment mechanism comprises a screw-thread on a holder tip, and a channel through the middle of the plug which provides both a sound pathway for sampling the noise level and a mechanism for attaching the holder tip to the plug.

5. The hearing protection device according to claim 3, wherein the compartment comprises a rear part that snap-fits to a front part.

6. The hearing protection device according to claim 5, wherein the rear part securely holds the microphone in place via a silicone ring.

7. The hearing protection device according to claim 6, wherein the rear part of the microphone holder assembly also provides a strain-relief to the microphone wire.

8. The hearing protection device according to claim 1, wherein the filter comprises three pieces of polyester cloth.

9. The hearing protection device of claim 1, wherein the microphone provides a flat response such that it captures all audible frequency components equally.

10. A hearing protection device to be worn at either a primary position or a secondary position, comprising a hearing protection component and a noise measurement component, wherein
    at the primary position the noise measurement component detects a protected noise exposure and at the secondary position it detects an unprotected noise exposure,
    the noise measurement component comprises a microphone, a microphone holder that encloses the microphone, at least one filter, and an attachment mechanism for removably attaching the noise measurement component to the hearing protection component;
    the hearing protection component comprises an insert-type earplug;
    the microphone holder comprises an acoustic duct having an exterior surface and an interior tube;
    the attachment mechanism comprises screw threads on the exterior surface of the acoustic duct;
    the interior tube of the acoustic duct serves as a channel through the middle of the earplug which provides a sound pathway for sampling noise exposure;
    the filter reduces resonance incident upon the microphone;
    the microphone holder further comprises a compartment for housing the microphone;
    the compartment is located exterior to the earplug;
    the microphone measures noise exposure via the interior tube; and
    the filter comprises one or more pieces of polyester cloth.

11. The hearing protection device of claim 10, wherein the noise measurement component further comprises a silicone ring that securely holds the microphone in place in the compartment.

12. The hearing protection device of claim 10, wherein the microphone comprises a face and the filter is located within the interior tube adjacent to the microphone to reduce reflection of sound away from the face of the microphone.

13. The hearing protection device of claim 10, wherein the microphone comprises a face and the filter is located within the microphone holder between the microphone and the interior tube to reduce reflection of sound away from the face of the microphone.

14. The hearing protection device of claim 10, wherein the microphone comprises a face directed towards the interior tube in order to measure sound waves via the acoustic duct, and the filter covers the face of the microphone to reduce reflection of sound away from the face of the microphone.

15. The hearing protection device of claim 14, wherein the filter comprises polyester cloth snuggly fit to the face of the microphone.

16. The hearing protection device of claim 14, wherein the filter minimizes resonance at a frequency of about 4.5 kHz without significantly attenuating other frequencies.

17. The hearing protection device of claim 10, wherein the filter minimizes resonance at a frequency of about 4.5 kHz without significantly attenuating other frequencies.

18. The hearing protection device of claim 17, wherein the filter comprises three or more pieces of polyester cloth snuggly fit to the face of the microphone.

19. The hearing protection device of claim 10, wherein the interior tube comprises an open end and a sealed end that is sealed by the microphone, the interior tube has a length of about 0.019 meters, and the filter decreases impendence of the sealed end of the interior tube.

20. The hearing protection device of claim 10, wherein the microphone provides a flat response.

* * * * *